United States Patent [19]

Jordan

[11] 4,034,037

[45] July 5, 1977

[54] CARBOXYLATION METALLATION PROCESS

[76] Inventor: Robert Kenneth Jordan, The Carlton House, Suite 1431, 550 Grant St., Pittsburgh, Pá. 15219

[22] Filed: Jan. 14, 1974

[21] Appl. No.: 433,296

[52] U.S. Cl. .................. 260/429 R; 260/414; 260/429.9; 260/430; 260/435 R; 260/438.1; 260/438.5 R; 260/439 R; 260/534 B; 260/541; 260/542; 260/553 C

[51] Int. Cl.² ................................ C07F 3/08

[58] Field of Search ........... 260/429 R, 430, 438.1, 260/435 R, 439 R, 438.5 R, 429.9, 534 B, 553 C, 541, 542, 414

[56] References Cited

UNITED STATES PATENTS

| | | | |
|---|---|---|---|
| 1,212,359 | 1/1917 | Katz et al. | 260/542 |
| 1,942,610 | 1/1934 | MacMullin | 260/534 B |
| 2,023,890 | 12/1935 | Kuss et al. | 260/429.9 X |
| 2,102,103 | 12/1937 | Urbain et al. | 260/541 |
| 2,957,826 | 10/1960 | Martinek | 252/33.6 |
| 3,056,820 | 10/1962 | Martinek | 260/429.7 |
| 3,518,286 | 6/1970 | Pande et al. | 260/429.7 |

OTHER PUBLICATIONS

Perkin et al., *Organic Chemistry*, W & R Chambers London, p. 148 (1907).
Mellor's *Modern Inorganic Chemistry*, Longmans, Green & Co., N. Y. p. 558.
Sudborough, *A Textbook of Organic Chemistry*, D. Van Nostrand Co. Inc. N. Y. p. 153.
*Chemical Abstracts*, vol. 52, 6995c (1958).
*Chemical Abstracts*, vol. 51, 3339f (1957).
*Chemical Abstracts*, vol. 58, 2376b (1963).

*Primary Examiner*—Helen M. S. Sneed

[57] ABSTRACT

A process for, and certain compositions of, the production of metal carboxylates or N-organic carbamates wherein the carboxylic acid or carbon dioxide and amine is converted to a solution of the corresponding ammonium carboxylate which in the presence of a soluble metal salt results in the precipitation of the product. Certain of these products are organic di and polycarbamic acid metal salts, new compositions of matter.

22 Claims, No Drawings

CARBOXYLATION METALLATION PROCESS

This invention relates to the production of precipitates of metal salts of organic carboxylates from an organic carboxylic acid or carbon dioxide, a metal salt of an acid stronger than carbonic acid and ammonia or an amine.

The metal salts of alkyl or aryl carboxylic acids have long been produced by a myriad of processes, so many processes that only the alkali metal salts of formic acid will be discussed in this introduction to the subject. Formic acid is most easily produced by the hydrolysis of methyl formate which in turn is made by the catalyzed addition of carbon monoxide to methanol. The ester can be treated directly with caustic soda resulting in saponification and a solution of sodium formate. In the practice of the production of alkali metal oxalates from alkali metal formates, the latter is made by treating aqueous sodium hydroxide with carbon monoxide. The resulting solution contains relatively dilute sodium formate and a little unreacted caustic soda. By evaporation and drying and then rapid heating to about 400° C the sodium formate is converted to sodium oxalate accompanied by the evolution of hydrogen. But the presence of caustic soda tends to lower the yield and the process of evaporation is expensive in terms of time and energy. When the sodium oxalate is dumped into water and treated with lime, a dilute solution of sodium hydroxide is recovered, evaporated to about 30—40 percent concentration and recycled in the process. The fact that the caustic must be recycled as opposed to being a product causes the process to be uneconomic.

Metal salts of N-substituted carbamic acids are practically unknown. This is surprising in view of the considerable volume of literature on the esters of N-substituted carbamic acids. This is probably due to the fact that no simple economic methods are reported for their production. The few references found give procedures utilizing metallic sodium or sodium hydride which are expensive as well as difficult to handle safely.

Therefore, it is an object of my invention to provide a new and improved process for the production of metal salts or organic carboxylates.

It is another object to provide a new and improved process for the production of metal formates.

It is a further object to provide a new and improved process for the production of N-organic substituted carbamic acid metal salts.

My invention is a process for, and certain compositions of, the production of metal carboxylates wherein an ammonium carboxylate is formed in a solution or slurry of at least one of mono-, bi- and tri-valent metal salts of nitric, nitrous, hydrochloric, hydrobromic, hydroiodic, perchloric, cyanic, sulfuric and prussic acids in an equivalent ratio of from about 0.1:1 to about 10:1 at a temperature in the range of from about −80° C to about 400° C.

I have discovered that the addition of ammonium formate to an equimolar amount of sodium chloride dissolved in liquid ammonia at −10° C results in the rapid precipitation of sodium formate in practically quantitative yield. The same result is had if formic acid is used in place of ammonium formate as the latter is formed. Similarly, other carboxylic salts of ammonia and primary, secondary and tertiary amines interact with dissolved metal salts to precipitate the corresponding metal carboxylate. Thus acetic, methacrylic, cyclohexanecarboxylic, maleic, benzoic and terephthalic acids participated in the same way yielding the metal salts as precipitates. Anhydrides gave lower yields in that they reacted with ammonia, or other amino compounds, to give the amide in addition to the ammonium salt. The amides do not give the corresponding metal salts in the process.

The production of sodium formate by the process of my invention is of significant importance from both the economic and technological points of view. The sodium formate precipitate can be readily washed free of ammonium chloride using a very small amount of ammonia without loss of product. As the sodium ion is derived directly from salt instead of the caustic soda normally used, a lower cost is realized, especially if the coproduct ammonium chloride is isolated and marketed. Moreover, the dry sodium formate as produced is of very high purity and can easily be fused to sodium oxalate in good yields. Also caustic soda can be produced as a coproduct as it does not need be recycled, greatly improving the economics of the oxalic acid process as well as providing a nonelectrolytic route to caustic soda. In a copending application I have disclosed a process for the production of carboxylic acid fluorides from the corresponding metal salts. A class of these carboxylic fluorides is the carbamoyl fluorides which can also be made form the corresponding metal carboxylate, but heretofore no economic route to these metal carboxylates has been known. By the use of a primary or secondary amine and carbon dioxide to form the corresponding ammonium carbamate in situ, my process readily converts the carboxylate to the metal carboxylate. Thus the addition of about an equivalent amount of methyl amine to a liquid ammonia solution of sodium chloride followed by the addition of less than an equivalent amount of carbon dioxide results in the immediate precipitation of the sodium salt of N-methyl carbamic acid. The identical product is had if methyl amine itself is used as the solvent. Dimethyl amine under exactly the same conditions gives a precipitate of N,N-dimethyl carbamic acid sodium salt. Thus it is possible to utilize a broad range of amines to produce mono- and di-substituted metal carbamates. Methylene diamine, n-butyl amine, hexamethylenediamine, cyclohexylamine, aniline, toluenediamine, monoethylaniline and methylenebis(4-aniline) are examples of the amines tested in the study.

Not all amines readily form the corresponding ammonium carbamates. Aromatic primary amines do so only under severe conditions such as carbon dioxide at high pressure and catalysts like those used for the production of formamide from carbon monoxide and ammonia. Alkyl aryl amines react more readily without catalysts and as noted, the alkyl primary and secondary amines very readily yield the desired carbamates.

Ideally the metal salts used in the process should be soluble in the media in which the process is conducted, but it has been found that in liquid ammonia salts with only slight solubility participate in the process to give precipitates of metal carboxylates. For converting the common carboxylic acids to their metal salts ammonia has been found to be a convenient and inexpensive media. It is also useful for producing the metal carbamates of amines which are stronger bases because of the higher solubility of the corresponding substituted ammonium salts in it as compared to the amine. The solubility of metal salts of acids in liquid ammonia provides a basis for a discussion of the scope of my process. Although solubility of the metal salt producing the cation for the metal carboxylate is not the the sole criteria of its utilization, it is important that the metal carboxylate be relatively insoluble, or capable of being easily salted out. The metal salts studied included those of sodium, potassium, magnesium, calcium, barium, iron II, iron III, nickel, manganese, chromium, cobalt, cadmium, zinc, copper I, copper II, silver and lead of nitric, nitrous, hydrochloric, hydrobromic, hydroiodic, perchloric, cyanic, thiocyanic, sulfuric, sulfurous and thiosulfuric acids and hydrogen cyanide in a number of media including liquid ammonia. The chlorides of most metals are only slightly soluble in liquid ammonia, sodium chloride is the outstanding exception reaching a maximum of 16 parts per hundred at $-10°$ C. But in liquid ammonia chlorides of metals having only slight solubility can cause the precipitation of the metal formate in the presence of ammonium formate although the rate is lower than obtained with more soluble salts. The bromides of most metals have fair solubililty and the iodides good solubility in liquid ammonia. The nitrites and nitrates have good solubility as do the cyanides, chlorates, thiocyanates and cyanates. It is interesting to note that a salt of every metal tried was found to yield the corresponding metal carboxylate. The fluorides, sulfates, sulfites and thiosulfates of ammonia and other metals are insoluble in liquid ammonia, but by the addition of water to the ammonia, products can be obtained from metal salts of these anions. Methanol is a fair solvent for the sulfates and sulfites, but again the media has to be used at relatively low temperature because the carboxylate of the metal is often fairly soluble at higher temperatures.

Effecting a clean separation of the product precipitated implies that the coproduct ammonium or substituted ammonium salt should have a high solubility in the media. The nitrates are preferred for this reason, also economically, for it is well known that nitric acid reacts with sodium chloride to give off hydrochloric acid or with potassium chloride to produce either hydrochloric acid or chlorine if oxygen is used in the process. Ammonium nitrate has a vast market as a nitrogenous fertilizer throughout the world. When producing carbamate metal salts by my process, the coproduct is the nitrate of the ammonium compound of the amine utilized in the system. For example, monomethyl amine would give methylammonium nitrate.

As noted, where possible ammonia is the preferred solvent for the process because many salts have some solubility in the media. But through the use of water and other diluents, many salts having practically no solubility in anhydrous liquid ammonia are quite soluble and participate in the process with rapidity. However, the solubility of the metal carboxylate must be taken into account when diluting the ammonia, amine, amide or other solvent used in the process. Also, carbamic acid metal salts are not stable in water, but it is surprising that by my process they have been made in 50:50 ammonia-water systems. The solubility of the metal carboxylate and the metal salt are the two principle considerations in solvent selection. Ideally the metal carboxylate should be relatively insoluble while it is desirable that the metal salt used should have some solubility. The use of ammonia-water systems allows operation at near atmospheric pressure. Various amines and formamide greatly extends the range in which the process can be conducted at atmospheric pressure, but as formamide only difficulty forms easily isolatable coproducts it is not normally useable as a substitute for ammonia. Other solvents useful in the process include acetonitrile, methanol, dimethyl formamide, acetamide, dimethyl sulfoxide, acetone, dioxane and benzene. Clearly other solvents and mixture not specifically noted here can be used.

The production of metal carbamates by my process can be accomplished through the use of ammonium or substituted ammonium carbamates that have been preformed. But it is far more expedient to produce the compound in situ by the addition of carbon dioxide or a carbon dioxide donating compound. Thus the addition of carbon dioxide to methyl amine yields methylammonium N-methylcarbamate as indicated in the following equation;

It is well known that anhydrous ammonia and carbon dioxide combine to give ammonium carbamate which can be used as a carbon dioxide donor with amines of greater basicity than ammonia. Carbon dioxide itself may be added in the form of a liquid, gas or solid.

A wide range of concentrations of the various intermediates can be utilized in the process without greatly affecting the yields. One significant limitation in the production of metal carbamates using liquid ammonia or another weaker amine as the solvent is that an excess of carbon dioxide will cause the precipitation of the metal salt of ammonium carbamate or of the carbamate of the weaker amine. When the product metal carboxylate has some solubility in the solvent employed, it may be desirable to use an excess of the salt to aid in salting out the product. Another factor may be the desire to obtain a high concentration of coproduct ammonium salt so that it can be readily crystallized from the media in which the process is conducted.

The process of my invention may be conducted over a wide range of temperatures and pressures. Even in liquid ammonia it is feasible to go well below $-50°$ C and up to it's critical temperature of about $117°$ C. Using formamide one can go above $300°$ C. Again using liquid ammonia the pressure can range from somewhat below atmospheric pressure to the critical pressure of ammonia. In making carbamates of aromatic amines it is often necessary to use high carbon dioxide pressures.

Whether producing metal salts of aliphatic or aryl carboxylic acids, or making the metal salts of organic substituted carbamic acids the crux of the invention is to produce an ammonium salt of the carboxylic acid which has at least some solubility in the media of the process and whose metal carboxylate is essentially less soluble in the same media. The metal salt employed as an intermediate in the process may have only slight solubility and yet produce the desired precipitate.

Only a relatively few metal salts of mono- and di-substituted carbamic acids have been reported in the literature and many of those reported were not proven or isolated. The process of my invention provides a wide range of new compounds in highly purified crystals, readily identifiable by hydrolysis and other techniques. U.S. Pat. No. 2,957,826 of Oct. 25, 1960 discloses compositions of the structure or composition of $M(NR_2CO_2)_x$ in which M is a metal ion of an alkali, alkaline earth, aluminum, tin or lead, $x$ is the valence of the metal, and R is hydrogen or a $C_{1-30}$ alkyl or aralkyl group. The sodium and potassium salts of carbanilic acid have long been known. By my process a considerable number of new metal salts of the composition of $M(NR_2CO_2)_r$ have been made, particularly of the transition metals and specifically of ferrous, ferric, nickel, cadmium, cobalt, zinc, cuprous, cupric, manganous and manganic of N-methyl carbamate. But even more useful are the new carbamates of the composition $(C_1R'_b)(NR''CO_2)_cM_d$ which in addition to being useful as fungicides and lubricant additives and insecticides are useful as intermediates for the production of isocyanates and carbamoyl fluorides by a process described in a copending application. In the composition $(C_aR'_b)(NR''CO_2)_cM_d$, R' and R'' are hydrogen, alkyl, aryl and halogen groups, M is a metal having a valence of from 1 to 3 inclusive, a may range from 1 to 50 and b from a-4 to 100, c from 2 to 5 and d from ⅔ to 5. A class of examples are the dicarbamic acid salts of methylene and polymethylene diamines. Those made include the sodium salts of the dicarbamic acids of methylene diamine, ethylene diamine and hexamethylene diamine. The dicarbamic acid salts of toluene diamine isomers, an 80:20 mixture of the 2,4- and 2,6- isomers, were made including the magnesium and potassium salts. Likewise the calcium salt of methylene bis(4-carbanilic acid) and the potassium salt of the dicarbamic acid based on the amine obtained by the hydrogenation of meta-xylene dinitrile which is made by the ammonoxidation of meta-xylene. Mixtures of the polyamines obtained by the acid condensation of aniline with formaldehyde were also converted to polycarbamic acid salts, but the components were not separated for identification.

The process of my invention is so readily made continuous that the subject needs only a cursory discussion. The metal salt in the form of a solid, slurry or solution may be added continuously to a solution of the ammonium or substituted ammonium carboxylate and held in a pipe or series of vessels for a given residence time at the appropriate temperature and then filtered or centrifuged continuously to remove the metal carboxylate product. The resulting liquor can be continuously separated by distillation or other treatment to remove the ammonium salt or regenerate the amine. Likewsie the ammonium carboxylate can be added to a solution or slurry of the metal salt and then processed in the same way. Clearly the acid or carbon dioxide may be continuously added to a solution or slurry containing ammonia or an amine and the metal salt and again processed in the same way.

According to the provision of the patent statutes, I have explained the principle of my invention and have illustrated and described what I now consider to represent its best embodiment. However, I desire to have it understood that within the scope of the appended claims, the invention may be practiced otherwise than as specifically illustrated and described.

I claim:

1. The compound of the formula $(R)(NR'CO_2)_cM_d$ where R is selected from alkylene containing 1 to 50 carbon atoms and arylene, R' is selected from the group consisting of hydrogen, alkyl and aryl, M is a metal having a valence of 1,2 or 3, c is from 2 to 5 and d is from two-thirds to 5.

2. The compound of claim 1 of methylenedicarbamic acid salts of alkali, alkaline earth and transition metals.

3. The compound of claim 1 of 1,6-hexamethylenedicarbamic acid salts of alkali, alkaline earth and transition metals.

4. The compound of claim 1 of methylenebis(4-carbanilic acid) salts of alkali, alkaline earth and transition metals.

5. The compounds of claim 1 of 2,4- and 2,6- toluenedicarbamic acid salts of alkali, alakline earth and transition metals.

6. The compounds of claim 1 of m-xylyldicarbamic acid salts of alkali, alkaline earth and transition metals.

7. A process for the production of metal carboxylates comprising combining an ammonium salt of a carboxylic acid and a metal salt of an acid in an inert solvent in an equivalent ratio of from about 0.1:1 to about 10:1 at a temperature in the range of from about −80° C to about 400° C.

8. The process of claim 7 wherein the solvent is selected from the group consisting of ammonia, formamide, acetamide, dimethyl formamide, acetonitrile, methanol, acetone, dioxane, ether and primary, secondary and tertiary amines wherein the concentration of the ammonium carboxylate and the metal salt is at least 0.1 weight percent.

9. The process of claim 7 wherein the solvent is ammonia containing water.

10. The process of claim 7 where the ammonium carboxylate is derived from a carboxylic acid selected from formic, alkyl, alkenyl, cycloalkyl, aralkyl, aryl, alkaryl and alkylenearylene mono-, di- and poly-carboxylic acids and ammonia, primary, secondary and tertiary amines.

11. The process of claim 7 wherein the ammonium salt of a carboxylic acid is ammonium formate and the metal salt of a mineral acid is sodium chloride in liquid ammonia.

12. A process for the production of metal carboxylates comprising combining a carboxylic acid with a metal salt of an acid and ammonia or an amine.

13. The process of claim 12 where the process is conducted in an inert solvent.

14. The process of claim 12 where the carboxylic acid is acetic acid, the metal salt of a mineral acid is sodium nitrate and ammonia is used.

15. A process for the production of metal N-organic substituted carbamates comprising an ammonium salt of an N-organic substituted carbamic acid and a metal salt of an acid an an inert solvent in an equivalent ratio for from about 0.1:1 to about 10:1 at a temperature in the range of from about −80° C to about 400° C.

16. The process of claim 15 wherein the solvent is selected from ammonia, formamide, acetamide, dimethylformamide, acetronitrile, methanol, acetone, dioxane, ether and primary, secondary and tertiary amines wherein the concentration of the ammonium carboxylate and the metal salt is at least 0.1 weight percent.

17. The process of claim 15 wherein the solvent is ammonia containing water.

18. The process of claim 15 where the ammonium salt of the N-substituted carbamic acid is selected from ammonium, primary, secondary and tertiary ammonium salts of alkyl, cycloalkyl, alkenyl, aralkyl, aryl, alkaryl, alkylenebisarylene and polyalkylenepolyarylene N-mono- and di- N-substituted mono-. di and polycarbamic acids.

19. The process of claim 15 where the ammonium salt of the N-organic substituted carbamic acid is the methylammonium salt of N-methyl carbamic acid and the metal salt of the mineral acid is sodium chloride in the inert solvent of ammonia.

20. A process for the production of metal N-organic substituted carbamates comprising combining carbon dioxide with a primary or secondary amine and a metal salt of an acid.

21. The process of claim 20 where the process is conducted in an inert solvent.

22. The process of claim 20 where the amine is methyl amine, the metal salt of a mineral acid is sodium chloride, and the inert solvent is ammonia.

* * * * *